United States Patent [19]
Carter

[11] Patent Number: 5,360,000
[45] Date of Patent: Nov. 1, 1994

[54] PNEUMATIC DEMAND OXYGEN VALVE

[75] Inventor: William Carter, Indianapolis, Ind.

[73] Assignee: Puritan-Bennett Corporation, Overland Park, Kans.

[21] Appl. No.: 13,226

[22] Filed: Feb. 1, 1993

Related U.S. Application Data

[63] Continuation of Ser. No. 787,775, Nov. 6, 1991, abandoned, which is a continuation of Ser. No. 680,028, Mar. 28, 1991, abandoned, which is a continuation of Ser. No. 305,446, Feb. 1, 1989, abandoned, which is a continuation of Ser. No. 27,943, Mar. 19, 1987, abandoned.

[51] Int. Cl.$^5$ .............................................. A61M 16/00
[52] U.S. Cl. ........................... 128/204.26; 128/205.24
[58] Field of Search ................. 128/201.28, 204.18, 128/204.26, 205.24; 251/28, 33, 43, 46; 137/489, 494, 908

[56] References Cited

U.S. PATENT DOCUMENTS

| | | | |
|---|---|---|---|
| 2,318,827 | 5/1943 | Yant | 128/204.26 |
| 2,552,595 | 5/1951 | Seezer | 128/204.26 |
| 3,285,261 | 11/1966 | Chaney | 128/204.26 |
| 3,434,471 | 3/1969 | Liston | 128/203.14 |
| 4,054,133 | 10/1977 | Myers | 128/204.26 |
| 4,575,042 | 3/1986 | Grimland et al. | 128/204.26 |

FOREIGN PATENT DOCUMENTS 8702590  3/1987  WIPO .......................... 128/204.26

OTHER PUBLICATIONS

Auerbach, David; "A New Oxygen Cannula System Using Intermittent-Demand Nasal Flow" Jul. 1, 1978.

Primary Examiner—Lee S. Cohen
Assistant Examiner—John P. Lacyk
Attorney, Agent, or Firm—Barnes & Thornburg

[57] ABSTRACT

A compact, simplified, totally pneumatic demand valve designed for coupling between a source of pressurized gas and a recipient user is provided which achieves a high degree of sensitivity and flow control without expensive, bulky valving arrangements characteristic of prior demand valves. Preferably, the demand valve includes a valve body presenting a gas flow passageway, together with pneumatically coupled sensing and slave diaphragms; the slave diaphragm is interposed in the flow passageway and prevents gas flow during the exhalation phases of the patient's breathing cycle. During inhalation sensed by the sensing diaphragm, the slave diaphragm is shifted to open the gas flow passageway in the valve, thus permitting passage of gas to the patient. The valve is designed for coupling to a fixed orifice flow controller, which may be positioned either downstream or upstream of the valve as desired.

27 Claims, 1 Drawing Sheet

PNEUMATIC DEMAND OXYGEN VALVE

This is a continuation of application Ser. No. 07/787,775, filed Nov. 6, 1991, now abandoned; which is a continuation of application Ser. No. 07/680,028, filed Mar. 28, 1991, now abandoned; which is a continuation of application Ser. No. 07/305,446, filed Feb. 1, 1989, now abandoned; which is a continuation of application Ser. No.07/027,943, filed Mar. 19, 1987, now abandoned.

BACKGROUND OF THE INVENTION

1. Field of the Invention

The present invention is broadly concerned with a demand-type pneumatic valve particularly adapted for administering medicinal gas, normally oxygen, to a patient undergoing respiratory therapy. More particularly, it is concerned with a compact, to tally pneumatic demand valve useful in a wide variety of contexts, including hospital, home care and ambulatory settings.

2. Description of the Prior Art

The traditional approach in administration of a medicinal gas such as oxygen is to connect the patient via a cannula to a source of pressurized gas, with the gas being administered on a more or less continuous basis. In the case of oxygen, however, studies have indicated that, in the continuous administration mode, significant quantities of oxygen are lost. That is to say, during the normal breathing cycle, the patient will inhale, exhale and pause before beginning the next inhalation; as a consequence, oxygen delivered to the patient during the exhale and pause portions of the breathing cycle are essentially wasted.

In response to this problem, it has been known in the past to provide valves of the so-called demand type, i.e., valves adapted to open only during the inspiration period of the patient's breathing cycle. Thus, U.S. Pat. No. 4,054,133 to Myers describes a demand-type valve of the pneumatic variety.

The Myers valve makes use of a sensing diaphragm arrangement made up of a pair of interconnected flexible diaphragms which cooperatively define a chamber. An adjustable spring engages one of these diaphragms in an attempt to provide a measure of sensitivity control. Moreover, the Myers device includes a rather complicated arrangement associated with the dual diaphragm structure designed to prevent the wastage of control volumes of gas, which typically may account for only 4 or 5% of the volume of gas used. As a consequence, the Myers design is inherently costly, and is believed prone to malfunction because of the inability to precisely respond to the changing pressure conditions induced during the patient's breathing cycle.

Thus, while the concept of a demand valve is known, there is a real and unsatisfied need in the art for a simplified, low cost, compact pneumatic demand valve.

SUMMARY OF THE INVENTION

The demand valve of the invention overcomes the noted difficulties and provides a greatly improved pneumatic demand valve designed for coupling between a source of pressurized gas, such as oxygen, and a breathing gas recipient, in order to supply gas to the recipient as needed on a demand basis. The demand valve broadly includes a body presenting a gas flow passageway there through having an inlet adapted for connection to the gas source and an outlet adapted for connection to the recipient. The valve body further has an internal sensing chamber having a port adapted for coupling to the recipient for transmission of the changing pressure conditions induced by the recipient's breathing to the sensing chamber. In practice, a dual lumen cannula is coupled to the device of the invention, with one of the lumen being a gas supply passageway for delivering quantities of oxygen on a demand basis. The remaining lumen is connected to the aforementioned sensing chamber port and leads to the nasal cavities of the patient, whereby to transmit to the sensing chamber the patient-induced pressure variations attendant to normal breathing.

The demand valve also includes sensing means in the form of only a single shiftable diaphragm operatively disposed in and forming a part of the sensing chamber and shiftable between a position corresponding to inhalation by the recipient, and a position corresponding to exhalation by the recipient. Such shifting is in response to the pressure conditions within the sensing chamber induced by the recipient's breathing and transmitted through the aforementioned cannula lumen.

The overall demand valve further includes a slave diaphragm operably interposed in the gas flow passageway and movable between a gas flow-blocking position and a gas flow-permitting position. In the gas flow-blocking position, the slave diaphragm engages an adjacent seat forming a part of the gas flow passageway through the body, and resists the forces exerted thereagainst by the pressurized gas. Means generally in the form of a small pilot passageway or orifice is provided for passing pressurized gas to a region adjacent the other face of the slave diaphragm, i.e., the face remote from that engageable with the passageway seat, so that the pressurized gas exerts pressure against both faces of the slave diaphragm.

Finally, the valve includes means operatively coupling the sensing diaphragm and the slave diaphragm for movement of the slave diaphragm from the flow-blocking position thereof to its flow-permitting position, in response to shifting of the sensing diaphragm from the exhalation to the inhalation positions thereof. Correspondingly, the coupling means provides for movement of the slave diaphragm from the flow-permitting to the flow-blocking positions thereof in response to shifting of the sensing diaphragm from the inhalation to the exhalation positions. This diaphragm coupling means preferably includes a port separate from the patient outlet and leading to the atmosphere for passage of pressurized gas from the region adjacent the other face of the s lave diaphragm to the atmosphere, upon shifting of the sensing diaphragm from the exhalation to the inhalation positions. Also, spring means is provided for engaging the slave diaphragm and biasing the same in a preselected direction. The combination of atmospheric venting and spring means serves to give precise coupling between the sensing and slave diaphragms.

In particularly preferred forms, the relief passageway is provided for communicating the adjacent faces of the sensing and slave diaphragms, with the relief passageway presenting a seat for engagement by the sensing diaphragm. Advantageously, the ratio between the effective area of the sensing diaphragm, and the effective area presented by the relief passageway seat, is at least about 35,000 to 1. This relatively large ratio is afforded by precision drilling of the appropriate relief passageway in the valve body, and makes it possible to significantly reduce the size of the overall valve while at the same time enhancing the sensitivity thereof. As used herein, the sensitivity of the valve apparatus refers to the pressure level required in the sensing cavity of the valve to induce movement of the sensing and slave diaphragms from a flow-preventing to a flow-permitting position.

DESCRIPTION OF THE PREFERRED EMBODIMENTS

Figure 1:
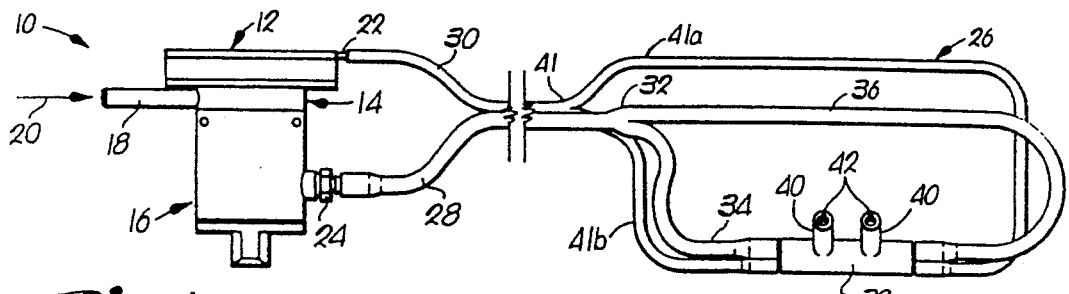
FIG. 1 is an elevational view with parts cut away showing a complete demand valve/flow controller in accordance with the invention, with a dual lumen cannula operatively coupled to the valve/flow controller apparatus.

Turning now to the drawing, a complete breathing assist apparatus 10 in accordance with the invention is illustrated in FIG. 1. Broadly speaking, the device 10 is in the form of a combined demand valve/flow controller unit 12 having a demand valve 14 operatively coupled with a selectable, multiple orifice flow controller 16. The demand valve includes an inlet 18 adapted for connection to a source of oxygen or other medicinal gas, illustrated by arrow 20. Valve 14 also has a sensing port 22 which is important for reasons to be described. The flow controller 16 on the other hand is of conventional construction and includes a gas outlet 24 adapted to supply gas to a recipient.

The overall assist apparatus 10 further includes a dual lumen cannula 26 having a pair of elongated flexible tubes in the form of a gas supply tube 28 and a sensing tube 30. The gas supply tube 28 is operatively connected to outlet 24 as shown, and, adjacent the recipient, divides at juncture 32 to present two branch legs 34, 36. The latter are interconnected by means of a nasal delivery structure 38 including a pair of spaced apart gas delivery tubes 40 respectively insertable into the patient's nasal cavities. The sensing tube 30 is operatively coupled to port 22 as depicted, and, adjacent the recipient, divides at juncture 41 to present two branch legs 41a and 41b; these legs are in turn connected to structure 38 as shown. A pair of short sensing tubes 42 are respectively located within the spaced delivery tubes 40 as shown, and these are coupled with the legs 41a, 41b. The function of sensing tube 30 is to convey and transmit, via the tubes 42 and the remainder of the tube body, the pressure conditions induced during the patient's breathing efforts, such pressure conditions being transmitted to port 22.

Figure 2:
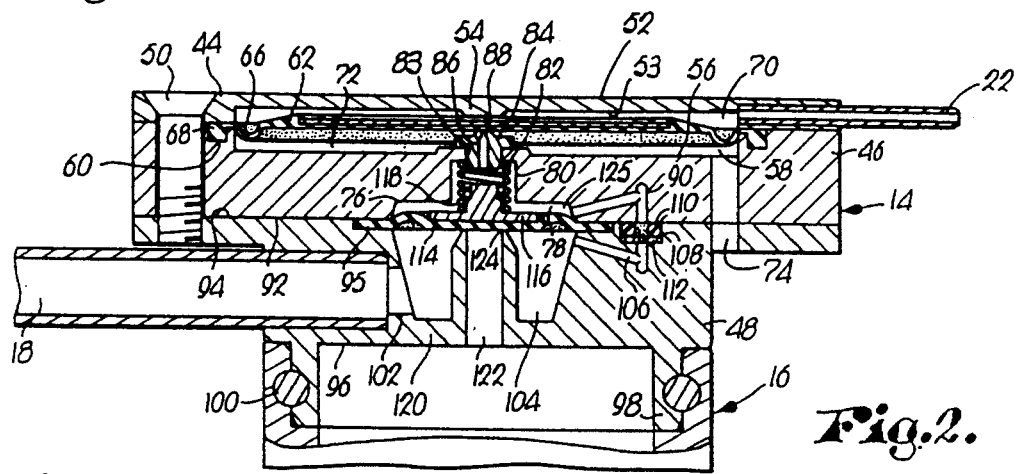
FIG. 2 is a fragmentary, enlarged view in vertical section illustrating the internal construction of the preferred demand valve.

Attention is next directed to FIG. 2 which illustrates in detail the preferred demand valve 14. Specifically, the valve 14 includes interconnected upper, intermediate and lower body components respectively numbered 44, 46 and 48. The components 44, 46, 48 are interconnected by means of screws 50 or other appropriate fasteners, in order to present a complete valve housing.

In more detail, it will be seen that the upper body component 44 is in the form of a substantially planar, circular in plan plate 52 presenting a lower chamber-defining wall surface 53 and a central, internal, depending stop 54. The righthand edge of plate 52 as shown in FIG. 2 is bored for reception of the elongated tubular port 22.

Intermediate body component 46 is designed to mate with upper component 44, and accordingly includes an upper wall surface 56 which, in conjunction with lower wall surface 53 of component 44, defines an internal recess 58. Furthermore, the intermediate component 46 includes a circular, essentially square in cross-section channel 60 in surrounding relationship to recess 58.

A sensing diaphragm 62 is located within recess 58 and is in the form of a circular, unbiased elastomeric body having a central reinforcing element therewithin, a downwardly extending, semicircular in cross-section, integral bead 66, and an essentially square in cross-section outermost peripheral connection rib 68. As illustrated, rib 68 is seated within channel 60, and the complete diaphragm 62 is maintained in position by virtue of the interconnection of the components 44, 46, serving to retain the peripheral connection bead 66.

The sensing diaphragm 62 in effect divides overall recess 58 into an upper sensing chamber 70 and a lower relief passageway 72. The port 22 is in communication with sensing chamber 70, whereas body component 44 is bored as at 74 to present an outlet or relief port communicating with passageway 72 and the atmosphere.

The intermediate body portion 46 is further provided with a central, stepped bore 76. The bore 76 presents a lowermost, radially expanded section 78, an upright spring-receiving section 80, and an uppermost section 82 presenting a bore 83 therethrough. An axially bored member 84 is seated within bore 83, with the bore 86 therethrough terminating in an uppermost restricted seat portion 88.

Finally, it will be observed that intermediate body portion 46 is provided with an angled bore 90 leading from expanded section 78 to the lower wall surface 92 presented by body component 46. The terminus of bore 90 is radially outwardly spaced from the expanded lower section 78 of bore 76, for reasons to be described.

The lower body component 48 includes an upper wall surface 94, an opposed lower surface 96, and a depending circular flange 98. The flange 98 is adapted to interfit with the upper end of flow controller 16 and to be connected thereto by means of fasteners 100.

The lower body component is provided with an inlet bore 102 adapted to receive the inlet tube 18. The inlet bore 102 in turn communicates with an upright, circular in cross-section pressurized gas chamber 104 which aligns with radially expanded section 78 of intermediate body component 44 as illustrated. An angled pilot bore 106 extends radially outwardly from the gas chamber 104 and terminates in opposed relationship to the end of bore 90 provided in intermediate body component 44. The upper wall surface 94 is relieved as at 108 and receives an O-ring 110 as well as an apertured metallic disc 112. In this fashion, compression of the body components 46, 48 serves to create a seal and hence a continuous gas flow passageway between chamber 104 and the expanded section of bore 76; the importance of the feature will be explained hereinafter.

The slave diaphragm 114 is situated atop and defines the upper surface of gas flow chamber 104. The diaphragm 114 includes an upstanding semicircular in cross-section marginal bead and is of elastomeric construction. The diaphragm 114 further is held in place by compression between the adjacent surfaces of body components 44, 46, and for this purpose, upper surface 94 of lower body component 48 is appropriately relieved as at 95 to receive the outermost marginal edge of the diaphragm 114.

A metallic actuator body 116 is in engagement with the upper surface of diaphragm 114 and includes an upright central section. A biasing spring 118 receiving the central section of the body 116 is interposed between the latter and the upper portion of body component 44 defining the aperture 82. This serves to bias diaphragm 114 downwardly as will be readily apparent.

The lower body component 48 has an innermost, central, upstanding, annular wall 120 which defines a central gas flow path 122 and an uppermost diaphragm seat 124 of reduced cross-sectional dimensions.

As noted, diaphragm 114 serves as the uppermost wall of gas chamber 104. This diaphragm also serves as the bottom or lower wall of a biasing chamber 125 defined by the stepped bore 76 and the diaphragm itself. Here again, the importance of this structure will be explained hereinafter.

The flow controller 16 is of entirely conventional design and provides a selector (not shown) for selecting any one of a number of differently sized, fixed dimension orifices which serve to deliver to the patient fixed rates of gas flow, e.g., 2, 4 or 6 liters per minute.

In overall context, it will thus be seen that the demand valve 14 presents a continuous gas flow passageway from the source of pressurized gas to the patient outlet. In particular, this passageway (see FIG. 3) is defined by the inlet 18, chamber 104 and flow path 122 leading to the flow controller 16 and ultimately outlet 24. Slave diaphragm 114 is operably interposed in this flow passageway, namely by engagement with the uppermost end of annular wall 120. Moreover, the sensing diaphragm 62 is pneumatically coupled with the slave diaphragm 114 for operation of the latter in response to operation of the sensing diaphragm.

Figure 3:
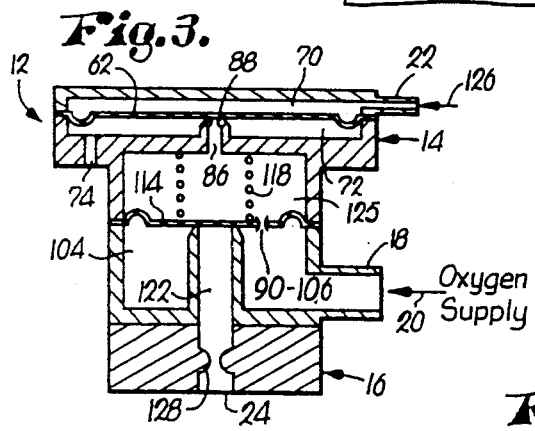
FIG. 3 is an essentially schematic, vertical sectional view depicting the preferred demand valve device, shown during exhalation.
Figure 4:
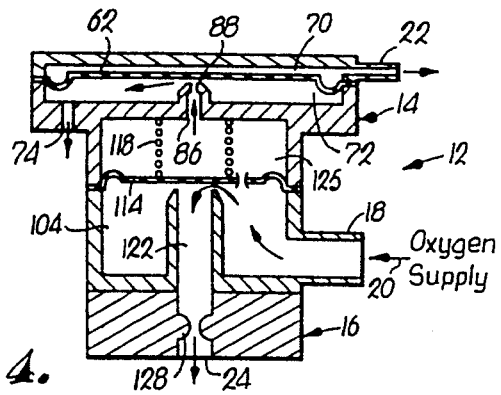
FIG. 4 is a view similar to that of FIG. 3, but showing the operation of the demand valve during inhalation.

In order to clearly explain the operation of demand valve 14, attention is directed to schematic FIGS. 3 and 4, which respectively show operation of the valve during exhalation and inhalation.

Thus, during exhalation (see FIG. 3), the pressure within sensing chamber 70 is positive, as indicated by arrow 126, such pressure conditions being induced by the patient and transmitted via cannula lumen 30 and port 22 from the patient. In this orientation, it will be seen that sensing diaphragm 62 is in engagement with the seat portion 88 of bore 86 thereby effecting a seal between biasing chamber 125 and relief passageway 72. The diaphragm 114 is retained in its sealing orientation by virtue of two factors, namely passage of gas from chamber 104 through the bores 90, 106 (shown for purposes of simplification in FIGS. 3 and 4 by means of pilot orifice 90/106 directly through the diaphragm itself) so as to substantially equalize pressure against both faces of the diaphragm 114, and the biasing of spring 118. Thus, pressure equalization is effected because of the pressurized gas acting simultaneously against both faces of diaphragm 114 during this sequence of operation, and this together with spring 118 closes the overall gas flow passageway through the demand valve 14.

During inhalation however (see FIG. 4), the negative pressure as indicated by arrow 127 induced within chamber 70 causes sensing diaphragm 62 to raise from engagement with seat 88. This establishes communication between biasing chamber 125 and relief passageway 72. As a consequence, the biasing gas within chamber 125 passes into the passageway 72 and is immediately exhausted to the atmosphere through communicating passageway 74. When this occurs, the pressure within chamber 104 is sufficient to raise slave diaphragm 114 from seat 124, thereby opening the gas flow passageway through the valve and permitting gas to travel from chamber 104 through flow path 122 and into flow controller 16. As described above, the flow controller 16 is of conventional design and includes selectable fixed orifice means schematically referred to by the throat 128; the flow controller creates, during inhalation, a fixed back pressure within the demand valve downstream of slave diaphragm 114.

Figure 5:
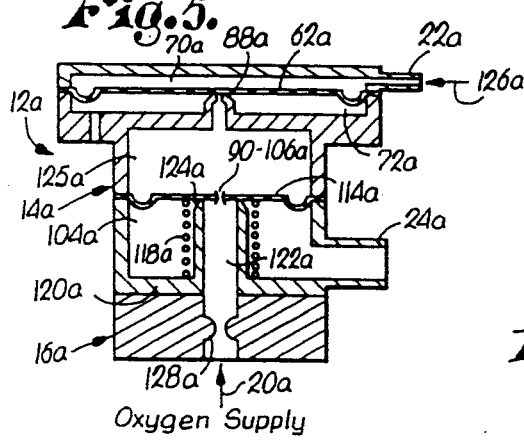
FIG. 5 is an essentially schematic, vertical sectional view illustrating another embodiment of the demand valve of the invention, shown during the exhalation phase of operation thereof.
Figure 6:
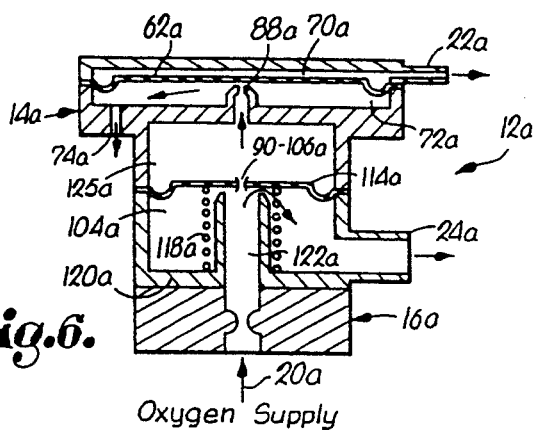
FIG. 6 is a view similar to that of FIG. 5, but showing the operation of the demand valve during inhalation.

FIGS. 5 and 6 illustrate another embodiment in accordance with the invention which is in many respects identical with that shown in FIGS. 3 and 4, and accordingly the same reference numerals are employed where appropriate, except with a letter designation "a". The principal difference between the embodiment of FIGS. 5 and 6 as compared with the preferred embodiment is that in the second embodiment the flow controller device 16a is upstream of the demand valve 14a. In order to provide this type of flow controller/demand valve orientation, the oxygen supply referred to by the arrow 20a first passes through the fixed throat 128a of the flow controller and thence into the path 122a of demand valve 14a. In terms of internal construction, the valve 14a is different in that the slave diaphragm 114a is inverted as compared with the embodiment of FIGS. 3–4, i.e., the marginal bead thereof opens upwardly as opposed to downwardly. Furthermore, the equalization orifice 90/106a is located in the center of the diaphragm and thus communicates with path 122a. Finally, in this orientation, it is necessary to position biasing spring 118a in surrounding relationship to the annular wall 120a so as to exert an upward biasing force against slave diaphragm 114a.

The operation of the embodiment of FIGS. 5–6 is in most respects identical to that described above. Thus, during the exhalation phase of operation illustrated in FIG. 5, the pressure conditions within sensing chamber 70a maintain diaphragm 62a in engagement with seat 88a. At this same time, pressurized gas is located within path 122a and biasing chamber 125a by virtue of pilot orifice 90/106a or its equivalent. This serves to maintain slave diaphragm 114a in engagement with seat 124a to prevent flow of gas to the patient.

When the patient inspires, the negative pressure within sensing chamber 70a causes diaphragm 62a to lift, whereby biasing gas within chamber 125a passes into passageway 72a and ultimately to the atmosphere through communicating passageway 74a. This creates an inequality of forces on the diaphragm 114a, whereby the latter is lifted thus opening the gas flow passageway through the valve 114a so that gas may pass through path 122a, chamber 104a and ultimately out the outlet 24a to the patient.

In both of the above described embodiments however, it will be seen that the sensing and slave diaphragms are pneumatically coupled for operation of the slave diaphragm in response to movement of the sensing diaphragm; the latter is in turn moved in response to the patient's breathing efforts as transmitted through the cannula.

A very desirable feature of the invention results from its fail safe characteristics. Specifically, a fail safe demand device is one that, upon a mechanical failure of one or more components, establishes a continuous flow of oxygen to be delivered to the recipient at the prescribed rate.

I claim:

1. An apparatus for controlling discharge of oxygen from an oxygen supply source to a patient through a breathing line coupled to the patient as the patient inhales and exhales, the apparatus comprising means for conducting oxygen provided by an oxygen supply source through a supply passageway having a gas inlet for attachment to an oxygen supply source and a gas outlet for attachment to a breathing line, the conducting means including a valve seat in the supply passageway, means for storing a supply of oxygen extant in the supply passageway in a first chamber to develop a pressure head in the first chamber, the storing means including inlet means for admitting oxygen from the supply passageway into the first chamber and outlet means for discharging oxygen from the first chamber to the atmosphere, means for selectively blocking flow of oxygen through the supply passageway from the gas inlet to the gas outlet, the blocking means including a flexible diaphragm valve member including a first side communicating with oxygen admitted into the first chamber and a second side facing the valve seat in the supply passageway, the diaphragm valve member being mounted for movement between a flow-blocking position engaging the valve seat in the supply passageway and a flow-delivery position disengaging the valve seat in the supply passageway, the blocking means further includes spring means for yieldably biasing the diaphragm valve member toward its flow-delivery position, the spring means lying in the supply passageway, and control means for closing the outlet means in response to exhalation of a patient breathing through the gas outlet to store pressurized oxygen in the first chamber so that oxygen pressure in the first chamber acting against the first side of the diaphragm valve member will increase to move the diaphragm valve member to its flow-blocking position and opening the outlet means in response to inhalation of a patient breathing through the gas outlet to vent pressurized oxygen in the first chamber to the atmosphere through the outlet means so that oxygen pressure in the first chamber will decrease to allow pressurized oxygen in the supply passageway to move the diaphragm valve member away from the valve seat to its flow-delivery position.

2. The apparatus of claim 1, wherein the spring means engages the second side of the diaphragm valve member.

3. The apparatus of claim 1, wherein the spring means includes a coiled spring and the coiled spring is arranged in the supply passageway to cause pressurized oxygen to pass through the coiled spring as it is conducted through the supply passageway from the gas inlet to the gas outlet.

4. The apparatus of claim 3, wherein the conducting means includes an elongated conduit formed to include a portion of the supply passageway, the elongated conduit includes an inlet end receiving oxygen provided through the gas inlet and an outlet end providing the valve seat, and the coiled spring winds around the elongated conduit.

5. The apparatus of claim 1, wherein the blocking means further includes spring means for urging the second side of the diaphragm valve member away from the valve seat in response to venting pressurized oxygen in the first chamber to the atmosphere through the outlet means.

6. The apparatus of claim 5, wherein the spring means engages the second side of the diaphragm valve member.

7. The apparatus of claim 5, wherein the spring means includes a coiled spring and the coiled spring is arranged in the supply passageway to cause pressurized oxygen to pass through the coiled spring as it is conducted through the supply passageway from the gas inlet to the gas outlet.

8. The apparatus of claim 7, wherein the conducting means includes an elongated conduit formed to include a portion of the supply passageway, the elongated conduit includes an inlet end receiving oxygen provided through the gas inlet and an outlet end providing the valve seat, and the coiled spring winds around the elongated conduit.

9. The apparatus of claim 1, wherein the flexible diaphragm valve member includes an annular perimetral edge and a circular body portion inside the perimetral edge, the circular body portion includes the first and second sides, and the circular body portion is arranged to position the first side in the first chamber and to position the second side in the supply passageway and in confronting relation to the valve seat in the supply passageway.

10. The apparatus of claim 9, wherein the circular body portion is made of elastomeric material and the second side of the circular body portion sealingly engages the valve seat upon movement of the diaphragm valve member to its flow-blocking position under a closing force applied to the first side of the circular body portion by pressurized oxygen in the first chamber.

11. The apparatus of claim 9, wherein the conducting means includes a housing, the housing is formed to include the first chamber and the supply passageway, the diaphragm valve member is arranged in the housing to define a partition between the first chamber and the supply passageway, and the annular perimetral edge is attached to the housing to support the circular body portion between the first chamber and the supply passageway to place the first side in communication with oxygen extant in the first chamber and the second side in communication with oxygen extant in the supply passageway.

12. The apparatus of claim 11, wherein the blocking means further includes spring means for yieldably biasing the diaphragm valve member toward its flow-delivery position and the spring means includes one end engaging the circular body portion and another end engaging the housing.

13. The apparatus of claim 11, wherein the spring means is a coil spring in the supply passageway and the coil spring includes one end engaging the second side of the diaphragm valve member and another end engaging the housing.

14. The apparatus of claim 11, wherein the conducting means includes an elongated conduit formed to include a portion of the supply conduit, the elongated conduit includes an inlet end receiving pressurized oxygen provided by the oxygen supply source and an outlet end providing the valve seat, the spring means is an elongated coil spring formed to include a hollow passageway extending therethrough, the elongated conduit extends through the hollow passageway in the coil spring, and the coil spring includes one end engaging the second side of the diaphragm valve member and another end engaging the housing.

15. The apparatus of claim 14, wherein the coil spring lies in the supply passageway in a position exposed to pressurized oxygen passing through the supply passageway.

16. The apparatus of claim 1, wherein the control means includes a vent passageway interconnecting the first chamber and the outlet means, a vent valve seat around the vent passageway, valve means for blocking flow of pressurized oxygen from the first chamber to the atmosphere through the outlet means, the valve means being mounted for movement between an opened position disengaging the vent valve seat and a closed position engaging the vent valve seat, and means defining a venting control chamber in communication with the valve means for receiving and using positive pressure generated by a patient exhaling into the gas outlet to exert a closing force on the valve means so that the valve means is moved to its closed position, thereby preventing venting of pressurized oxygen in the first chamber to the atmosphere through the outlet means.

17. An apparatus for controlling discharge of oxygen from an oxygen supply source to a patient through a breathing line coupled to the patient as the patient inhales and exhales, the apparatus comprising means for conducting oxygen provided by an oxygen supply source through a supply passageway having a gas inlet for attachment to an oxygen supply source and a gas outlet for attachment to a breathing line, the conducting means including a valve seat in the supply passageway, means for storing a supply of oxygen extant in the supply passageway in a first chamber to develop a pressure head in the first chamber, the storing means including inlet means for admitting oxygen from the supply passageway into the first chamber and outlet means for discharging oxygen from the first chamber to the atmosphere, means for selectively blocking flow of oxygen through the supply passageway from the gas inlet to the gas outlet, the blocking means including a flexible diaphragm valve member including a first side communicating with oxygen admitted into the first chamber and a second side facing the valve seat in the supply passageway, the diaphragm valve member being mounted for movement between a flow-blocking position engaging the valve seat in the supply passageway and a flow-delivery position disengaging the valve seat in the supply passageway, and control means for closing the outlet means in response to exhalation of a patient breathing through the gas outlet to store pressurized oxygen in the first chamber so that oxygen pressure in the first chamber acting against the first side of the diaphragm valve member will increase to move the diaphragm valve member to its flow-blocking position and opening the outlet means in response to inhalation of a patient breathing through the gas outlet to vent pressurized oxygen in the first chamber to the atmosphere through the outlet means so that oxygen pressure in the first chamber will decrease to allow pressurized oxygen in the supply passageway to move the diaphragm valve member away from the valve seat to its flow-delivery position, the blocking means further includes spring means for yieldably biasing the diaphragm valve member toward its flow-blocking position and the spring means lies in the first chamber.

18. The apparatus of claim 17, wherein the spring means engages the first side of the diaphragm valve member.

19. An apparatus for controlling discharge of oxygen from an oxygen supply source to a patient through a breathing line coupled to the patient as the patient inhales and exhales, the apparatus comprising means for conducting oxygen provided by an oxygen supply source through a supply passageway having a gas inlet for attachment to an oxygen supply source and a gas outlet for attachment to a breathing line, the conducting means including a valve seat in the supply passageway, means for storing a supply of oxygen extant in the supply passageway in a first chamber to develop a pressure head in the first chamber, the storing means including inlet means for admitting oxygen from the supply passageway into the first chamber and outlet means for discharging oxygen from the first chamber to the atmosphere, means for selectively blocking flow of oxygen through the supply passageway from the gas inlet to the gas outlet, the blocking means including a flexible diaphragm valve member including a first side communicating with oxygen admitted into the first chamber and a second side facing the valve seat in the supply passageway, the diaphragm valve member being mounted for movement between a flow-blocking position engaging the valve seat in the supply passageway and a flow-delivery position disengaging the valve seat in the supply passageway, and control means for closing the outlet means in response to exhalation of a patient breathing through the gas outlet to store pressurized oxygen in the first chamber so that oxygen pressure in the first chamber acting against the first side of the diaphragm valve member will increase to move the diaphragm valve member to its flow-blocking position and opening the outlet means in response to inhalation of a patient breathing through the gas outlet to vent pressurized oxygen in the first chamber to the atmosphere through the outlet means so that oxygen pressure in the first chamber will decrease to allow pressurized oxygen in the supply passageway to move the diaphragm valve member away from the valve seat to its flow-delivery position, the inlet means being formed to include a bypass passageway communicating pressurized oxygen from the supply passageway to the first chamber and including a disk placed in the bypass passageway and formed to include aperture means for reducing flow rate of pressurized oxygen delivered to the first chamber through the bypass passageway.

20. The apparatus of claim 19, wherein the apparatus further comprises a housing formed to include the conducting means, the storing means, and disk-receiving means for receiving the disk in the bypass passageway to orient the disk so that it partitions the bypass passageway into an oxygen-conducting upstream portion communicating with the supply passageway and an oxygen-conducting downstream portion communicating with the first chamber and positions the aperture means to lie in the bypass passageway and interconnect the oxygen-conducting upstream and downstream portions in fluid communication.

21. The apparatus of claim 20, wherein the housing includes a first body, a second body, and means for joining the bodies together at a parting line to form a unit, the first body is formed to include the supply passageway and at least a portion of the oxygen-conducting upstream passageway, the second body is formed to include the first chamber and the oxygen-conducting downstream passageway, and the disk-receiving means is located in the housing and formed to include a disk-receiving opening at the parting line that is exposed to receive a disk therein upon separation of the first and second bodies at the parting line.

22. An apparatus for controlling discharge of oxygen from an oxygen supply source to a patient through a breathing line coupled to the patient as the patient inhales and exhales, the apparatus comprising means for conducting oxygen provided by an oxygen supply source through a supply passageway having a gas inlet for attachment to an oxygen supply source and a gas outlet for attachment to a breathing line, the conducting means including a valve seat in the supply passageway, means for storing a supply of oxygen extant in the supply passageway in a first chamber to develop a pressure head in the first chamber, the storing means including inlet means for diverting pressurized oxygen from the supply passageway into the first chamber through a bypass passageway, a disk mounted in the bypass passageway and formed to include aperture means for reducing flow rate of pressurized oxygen delivered to the first chamber through the bypass passageway, and outlet means for discharging oxygen from the first chamber to the atmosphere, means for selectively blocking flow of oxygen through the supply passageway from the gas inlet to the gas outlet, the blocking means being mounted for movement between a flow-blocking position engaging the valve seat in the supply passageway and a flow-delivery position disengaging the valve seat in the supply passageway, and control means for closing the outlet means in response to exhalation of a patient breathing through the gas outlet to store pressurized oxygen in the first chamber so that oxygen pressure in the first chamber acting against the blocking means will increase to move the blocking means to its flow-blocking position and opening the outlet means in response to inhalation of a patient breathing through the gas outlet to vent oxygen in the first chamber to the atmosphere through the outlet means so that pressure in the first chamber will decrease to allow pressurized oxygen in the supply passageway to move the blocking means away from the valve seat to its flow-delivery position.

23. The apparatus of claim 22, wherein the apparatus further comprises a housing formed to include the conducting means, the storing means, and disk-receiving means for receiving the disk in the bypass passageway to orient the disk so that it partitions the bypass passageway into an oxygen-conducting upstream portion communicating with the supply passageway and an oxygen-conducting downstream portion communicating with the first chamber and positions the aperture means to lie in the bypass passageway and interconnect the oxygen-conducting upstream and downstream portions in fluid communication.

24. The apparatus of claim 23, wherein the housing includes a first body, a second body, and means for joining the bodies together at a parting line to form a unit, the first body is formed to include the supply passageway and at least a portion of the oxygen-conducting upstream passageway, the second body is formed to include the first chamber and the oxygen-conducting downstream passageway, and the disk-receiving means is located in the housing and formed to include a disk-receiving opening at the parting line that is exposed to receive the disk therein upon separation of the first and second bodies at the parting line.

25. The apparatus of claim 22, wherein the blocking means includes a movable flexible diaphragm valve member including a first side communicating with oxygen diverted into the first chamber and a second side facing the valve seat in the supply passageway.

26. The apparatus of claim 22, wherein the control means includes a vent passageway interconnecting the first chamber and the outlet means, a vent valve seat around the vent passageway, valve means for blocking flow of pressurized oxygen from the first chamber to the atmosphere through the outlet means, the valve means being mounted for movement between an opened position disengaging the vent valve seat and a closed position engaging the vent valve seat, and means defining a venting control chamber in communication with the valve means for receiving and using positive pressure generated by a patient exhaling into the breathing line to exert a closing force on the valve means so that the valve means is moved to its closed position, thereby preventing venting of pressurized oxygen in the first chamber to the atmosphere through the outlet means.

27. The apparatus of claim 26, wherein the valve means includes a sensing diaphragm movable to engage and disengage the vent valve seat and the ratio between the effective area of the sensing diaphragm and the effective area presented by the vent valve seat is about 35,000 to 1.

* * * * *